United States Patent
Izawa et al.

(10) Patent No.: US 10,485,255 B2
(45) Date of Patent: Nov. 26, 2019

(54) **CULTURE PRODUCT OF MICROORGANISM BELONGING TO THE GENUS *WICKERHAMOMYCES***

(71) Applicant: KABUSHIKI KAISHA YAKULT HONSHA, Minato-ku (JP)

(72) Inventors: Naoki Izawa, Minatu-ku (JP); Miyuki Kudo, Minato-ku (JP); Toshiro Sone, Minato-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 18 days.

(21) Appl. No.: 15/544,435

(22) PCT Filed: Jan. 18, 2016

(86) PCT No.: PCT/JP2016/051232
§ 371 (c)(1),
(2) Date: Jul. 18, 2017

(87) PCT Pub. No.: WO2016/117489
PCT Pub. Date: Jul. 28, 2016

(65) Prior Publication Data
US 2018/0000139 A1 Jan. 4, 2018

(30) Foreign Application Priority Data
Jan. 19, 2015 (JP) ................. 2015-008129

(51) Int. Cl.
| | | |
|---|---|---|
| *A23L 27/10* | (2016.01) | |
| *C12P 1/02* | (2006.01) | |
| *C12P 7/62* | (2006.01) | |
| *A61K 8/99* | (2017.01) | |
| *A61K 36/062* | (2006.01) | |
| *A61Q 13/00* | (2006.01) | |
| *C12N 1/16* | (2006.01) | |
| *C11B 9/00* | (2006.01) | |
| *A23L 27/20* | (2016.01) | |
| *A61K 8/98* | (2006.01) | |
| *A61Q 1/00* | (2006.01) | |
| *A23L 2/54* | (2006.01) | |
| *A23L 27/24* | (2016.01) | |
| *A61C 19/00* | (2006.01) | |
| *A23L 27/29* | (2016.01) | |
| *A23L 31/15* | (2016.01) | |
| *A61K 8/9728* | (2017.01) | |
| *A61K 36/064* | (2006.01) | |
| *C12R 1/645* | (2006.01) | |

(52) U.S. Cl.
CPC .............. *A23L 27/10* (2016.08); *A23L 2/54* (2013.01); *A23L 27/204* (2016.08); *A23L 27/24* (2016.08); *A23L 27/29* (2016.08); *A23L 31/15* (2016.08); *A61C 19/00* (2013.01); *A61K 8/9728* (2017.08); *A61K 8/986* (2013.01); *A61K 8/99* (2013.01); *A61K 36/062* (2013.01); *A61K 36/064* (2013.01); *A61Q 1/00* (2013.01); *A61Q 13/00* (2013.01); *C11B 9/0003* (2013.01); *C11B 9/0061* (2013.01); *C12N 1/16* (2013.01); *C12P 1/02* (2013.01); *C12P 7/62* (2013.01); *A23V 2002/00* (2013.01); *C12R 1/645* (2013.01)

(58) Field of Classification Search
None
See application file for complete search history.

(56) References Cited

U.S. PATENT DOCUMENTS

2013/0017587 A1* 1/2013 Nierlich .................. C12P 7/04
435/158

FOREIGN PATENT DOCUMENTS

| | | |
|---|---|---|
| JP | 5-49465 A | 3/1993 |
| JP | 2001-103959 A | 4/2001 |
| JP | 2005-15686 A | 1/2005 |
| JP | 2012-55286 A | 3/2012 |

OTHER PUBLICATIONS

Chaves-Lopez et al., Int. J. Food Microbiol. 159: 39-46 (2012).*
Imanishi et al., Microbiology 155: 3142-3148 (2009).*
Wibbertmann et al., "Concise International Chemical Assessment Document 26: Benzoic Acid and Sodium Benzoate", World Health Organization, 2000 (https://www.who.int/ipcs/publications/cicad/cicad26_rev_1.pdf).*
S. Chen, et al. "The Influence of Yeast Strains on the Volatile Flavour Compounds of Chinese Rice Wine," Journal of the Institute of Brewing, 2010, vol. 116, No. 2, pp. 190-196.
Y. Imanishi, et al., "Mode of vegetative reproduction of the bipolar budding yeast species *Wickerhamomyces pijperi* and related strains," Microbiology, 2009, vol. 155, pp. 3142-3148.
C. Chaves-Lopez, et al., "Yeasts from Colombian Kumis as source of peptides with Angiotensin I converting enzyme (ACE) inhibitory activity in milk," International Journal of Food Microbiology, 2012, vol. 159, pp. 39-46.

(Continued)

*Primary Examiner* — Erin M. Bowers
(74) *Attorney, Agent, or Firm* — Oblon, McClelland, Maier & Neustadt, L.L.P.

(57) ABSTRACT

A culture product comprising a large quantity of ethyl benzoate and has a more complex and fresher fruity aroma than a chemically synthesized product.

The culture product is obtained by culturing a microorganism belonging to the genus *Wickerhamomyces* in a milk component-containing culture medium.

12 Claims, No Drawings

(56) References Cited

OTHER PUBLICATIONS

V. R. Suriyarachchi, et al., "Occurrence and Growth of Yeasts in Yogurts," Applied and Environmental Microbiology, Oct. 1981, vol. 42, No. 3, pp. 574-579.

R. Sieber, et al., "Benzoic Acid as a Natural Compound in Cultured Dairy Products and Cheese," International Dairy Journal, 1995, vol. 5, pp. 227-246.

D. Dimitrellou, et al., "Whey-cheese production using freeze-dried kefir culture as a starter," Journal of Applied Microbiology, 2007, vol. 103, pp. 1170-1183.

J. Khatabiah, et al., "Efficacy of Benzoate and Sorbate on the Growth Control of Total and Psychrotrophic Yeasts in Labneh," Egyptian Journal of Dairy Science, 2012, vol. 40, pp. 35-43.

N. Izawa, et al., "Production of aroma compounds from whey using *Wickerhamomyces pijperi*," AMB Express, 2015, vol. 5, No. 23, 9 pages.

N. Izawa, et al., "Effects of fermentation conditions on aroma compounds production by *Wickerhamomyces pijperi*," vol. 67, 2015, (with partial English translation of relevant text), 5 pages.

International Search Report dated Mar. 22, 2016 in PCT/JP2016/051232 filed Jan. 18, 2016.

\* cited by examiner

CULTURE PRODUCT OF MICROORGANISM BELONGING TO THE GENUS WICKERHAMOMYCES

FIELD OF THE INVENTION

The present invention relates to a culture product having a good aroma and its use.

BACKGROUND OF THE INVENTION

A method for obtaining a culture product having a good aroma by using a yeast that produces various aroma components, for example, *Saccharomyces cerevisiae* has been conventionally known, and the culture product thus obtained has been used for food and drink (Patent Literatures 1 to 3).

Ethyl benzoate, which is one of aroma components, can be chemically synthesized from benzoic acid and ethanol. This compound is known as one of the aroma components of a star fruit and has been industrially used as an artificial flavor giving an aroma of a fruit. A culture product which is obtained by using *Saccharomyces cerevisiae* and contains ethyl benzoate as an aroma component is known; however, the content of ethyl benzoate was as low as from 0.006 to 0.009 ppm (Non Patent Literature 1).

*Wickerhamomyces pijperi* is a yeast which was formerly referred to as *Pichia pijperi* and reclassified as *Wickerhamomyces pijperi*. Non Patent Literature 2 describes culturing this yeast in a yeast extract-mannitol culture medium and a yeast-peptone-dextrose (YPD) culture medium; however, the characteristic of the culture product thus obtained was unknown and neither of the possibility of culturing *Wickerhamomyces pijperi* in a milk component-containing culture medium and the aroma of the resulting culture product was totally unknown.

CITATION LIST

Patent Literature

Patent Literature 1: JP-A-H5-49465
Patent Literature 2: JP-A-2001-103959
Patent Literature 3: JP-A-2012-55286

Non Patent Literature

Non Patent Literature 1: Journal of the Institute of Brewing, 116, 190-196, 2010
Non Patent Literature 2: Microbiology, 155, 3142-3148, 2009

SUMMARY OF THE INVENTION

Problems to be Solved by the Invention

A chemically synthesized product of the above described aroma component such as ethyl benzoate has a bland odor and has not been necessarily satisfactory if incorporated in a flavoring composition. Therefore, there has been a need for provision of a composition which can be used for a cosmetic product, a food or a drink, and a pharmaceutical product, has a more palatable aroma than a chemically synthesized product, and can be used as a flavoring composition. Furthermore, many consumers like a fruity aroma and thus there has been a need for provision of a novel fruity aroma.

It is an object of the present invention to provide a novel composition which can be used for a flavoring composition, a cosmetic product, a food or a drink, a pharmaceutical product, and the like, wherein the composition contains a large quantity of ethyl benzoate and has a more complex and fresher fruity aroma than a chemically synthesized product of ethyl benzoate; and the use thereof.

Means for Solving the Problems

Thus, the present inventors carried out extensive studies to develop a composition having a good aroma and totally surprisingly have found out the following facts: a culture product is obtained which contains a large quantity of ethyl benzoate known as an aroma component and has a more complex and fresher fruity aroma than a chemically synthesized product of ethyl benzoate when a microorganism belonging to the genus *Wickerhamomyces* is cultured in a milk component-containing culture medium; and this culture product is useful as a culture product which can be used for a flavoring composition, a cosmetic product, a food or a drink, a pharmaceutical product, and the like, and accomplished the present invention.

Specifically, the present invention provides the following [1] to [10]:

[1] A culture product obtained by culturing a microorganism belonging to the genus *Wickerhamomyces* in a milk component-containing culture medium.
[2] The culture product according to [1], wherein the milk component-containing culture medium is a whey-containing culture medium.
[3] The culture product according to [1] or [2], wherein the microorganism belonging to the genus *Wickerhamomyces* is *Wickerhamomyces pijperi*.
[4] The culture product according to any of [1] to [3], wherein the microorganism belonging to the genus *Wickerhamomyces* is *Wickerhamomyces pijperi* NBRC1290 and/or *Wickerhamomyces pijperi* NBRC1887.
[5] The culture product according to any of [1] to [4], wherein the milk component-containing culture medium further contains benzoic acid and/or a salt thereof.
[6] A flavoring composition comprising the culture product according to any of [1] to [5].
[7] A cosmetic product comprising the culture product according to any of [1] to [5].
[8] A food or a drink comprising the culture product according to any of [1] to [5].
[9] A pharmaceutical product comprising the culture product according to any of [1] to [5].
[10] A method for imparting an aroma to a cosmetic product, a food or a drink, or a pharmaceutical product, comprising adding the culture product according to any of [1] to [5] thereto.

Effects of the Invention

The culture product of the present invention contains a large quantity of ethyl benzoate and has a more complex and fresher fruity aroma than a chemically synthesized product of ethyl benzoate. Therefore, the culture product is useful as a culture product used for not only a flavoring composition and a cosmetic product but also a food or a drink and a pharmaceutical product.

Modes for Carrying Out the Invention

The culture product of the present invention is a culture product obtained by culturing a microorganism belonging to the genus *Wickerhamomyces* in a milk component-containing culture medium.

Examples of the microorganism belonging to the genus *Wickerhamomyces* include *Wickerhamomyces pijperi*, *Wickerhamomyces anomalus*, *Wickerhamomyces bovis*, *Wickerhamomyces rabaulensis*, *Wickerhamomyces hampshirensis*, *Wickerhamomyces strasburgensis*, *Wickerhamomyces sydowiorum*, *Wickerhamomyces lynferdii*, *Wickerhamomyces ciferrii*, *Wickerhamomyces chambardii*, *Wickerhamomyces silvicola*, *Wickerhamomyces bisporus*, *Wickerhamomyces alni*, *Wickerhamomyces canadensis*, *Wickerhamomyces onychis*, *Wickerhamomyces edaphicus*, and *Wickerhamomyces patagonicus*. *Wickerhamomyces pijperi* is preferable among them. Furthermore, among *Wickerhamomyces pijperi* strains, NBRC1290 and NBRC1887 deposited at NBRC (NITE Biological Resource Center) are more preferable. These microorganisms may be used alone or these microorganisms may be used in combination. In this context, the microorganism which was formerly classified as *Pichia pijperi* and can be reclassified as *Wickerhamomyces pijperi* is included under *Wickerhamomyces pijperi* of the present application.

As used herein, "milk component" refers to raw milk, heat-treated milk, skimmed milk powder, or whole milk powder of animal's milk such as cow milk, goat milk, and sheep milk, or a material containing a milk-derived component, such as fresh cream and whey.

The milk component-containing culture medium may be any culture medium containing a milk component and may further contain other components. Preferable examples of such other components include, but not particularly limited to, a sugar such as glucose, galactose, lactose, and fructose, and benzoic acid and/or a salt thereof. A preferable sugar is glucose in that glucose is utilized as an energy source by a microorganism. Benzoic acid and/or a salt thereof are preferable in that the addition thereof enhances the yield of ethyl benzoate by a microorganism. A salt of benzoic acid is more preferably an alkali metal salt of benzoic acid such as sodium benzoate and potassium benzoate, and even more preferably sodium benzoate. Thus, it is preferable to add benzoic acid and/or sodium benzoate as benzoic acid and/or a salt thereof.

A particularly preferable milk component is whey since whey enhances the yield of ethyl benzoate by a microorganism. "Whey" is the part obtained after removing milk fat and casein from milk. For example, whey can be obtained as a culture supernatant when a milk component was fermented by a microorganism, and preferably contains a sugar such as lactose and galactose, an amino acid, lactic acid, a protein, and the like.

Furthermore, whey is preferably a culture supernatant obtained when a milk component was cultured particularly by a lactic acid *bacterium* and/or a *bifidobacterium*. In this context, examples of the lactic acid *bacterium* and/or the *bifidobacterium* may include a *Lactobacillus bacterium* such as *Lactobacillus casei*, *Lactobacillus mali*, *Lactobacillus acidophilus*, *Lactobacillus delbrueckii* subsp. *bulgaricus*, and *Lactobacillus helveticus*; a *Streptococcus bacterium* such as *Streptococcus thermophilus*; a *Lactococcus bacterium* such as *Lactococcus lactis* subsp. *lactis* and *Lactococcus lactis* subsp. *cremoris*; an *Enterococcus bacterium* such as *Enterococcus faecalis*; and a *Bifidobacterium bacterium* such as *Bifidobacterium breve*, *Bifidobacterium bifidum*, and *Bifidobacterium longum*.

The content of the milk component in a culture medium is, but not particularly limited to, preferably from 1 to 50% by mass (hereinafter, referred to simply as "%") and more preferably from 2 to 10% in terms of a solid content. The content of benzoic acid and/or a salt thereof in the milk component-containing culture medium is preferably from 0.001 to 0.1% and more preferably from 0.01 to 0.05% from a point of view of the yield of ethyl benzoate by a microorganism and the growth potential of the microorganism. The content of glucose is preferably from 0.1 to 10% and more preferably from 1 to 5% from a point of view of the growth potential of the microorganism.

The temperature for culturing the microorganism belonging to the genus *Wickerhamomyces* is, but not particularly limited to, preferably from 15 to 30° C. and more preferably from 20 to 30° C. from a point of view of the aroma of the culture product. The culture time is preferably 8 hours or more, and more preferably from 24 to 32 hours. When benzoic acid and/or a salt thereof are added to the culture medium, the culture time is preferably from 24 to 48 hours, and more preferably from 32 to 48 hours. Examples of the culture method include shaking culture, static culture, shake culture, and culture at neutral pH.

The culture product of the present invention contains 1.0 ppm or more of ethyl benzoate and has a more complex and fresher fruity aroma than a chemically synthesized product of ethyl benzoate. The content of ethyl benzoate is preferably from 1.0 to 50 ppm, and more preferably from 1.0 to 30 ppm.

Furthermore, the culture product of the present invention may contain other aroma components other than ethyl benzoate. Examples of the other aroma components include an aroma component such as isoamyl alcohol.

The culture product of the present invention contains a large quantity of ethyl benzoate and has a good, more complex and fresher fruity aroma than a chemically synthesized product of ethyl benzoate, and therefore, can be used for a flavoring composition, a cosmetic product, a food or a drink, a pharmaceutical product, and the like. The culture product can be used favorably for a cosmetic product, since there are not many biological flavors industrially available in the cosmetic field and the demand for a natural flavor is higher than that for a synthetic flavor.

The culture product of the present invention may be added to a flavoring composition, a cosmetic product, a food or a drink, a pharmaceutical product, and the like as it is, but the culture product is preferably added after filtration. Furthermore, the culture product may be concentrated by lyophilization, distillation, or the like, and the resulting concentrate may be added to a flavoring composition, a cosmetic product, a food or a drink, a pharmaceutical product, and the like.

Examples of the cosmetic product include an aromatic cosmetic product such as a perfume, an eau de cologne, and an eau de toilette; a basic skincare product such as a toner, a milky lotion, a lotion, a cream, a facial mask, and a serum; a haircare product such as a shampoo and a conditioner; a bath cosmetic product such as a bath additive; a makeup product such as a foundation; and a special cosmetic product such as a sunscreen. Examples of the food or a drink include various types of refreshing drinks, a sparkling liquor, a beer, a refined sake, confectionery, ices, an ice cream, and dairy products such as a fermented milk. Examples of the pharmaceutical product include an external preparation such as a cream, an ointment, and a gel. The content of the culture product of the present invention in such a cosmetic product, a food or a drink, and a pharmaceutical product is preferably from 0.01 to 10% and more preferably from 0.1 to 1% in terms of a solid content.

EXAMPLES

The present invention will now be described in detail by way of Examples.

Example 1

(1) Strains and Pre-Preculture
  (i) Used Strains

*Wickerhamomyces pijperi* YIT8095 (NBRC1290), *Wickerhamomyces pijperi* YIT12779 (NBRC1887)

Comparative Example: *Kluyveromyces marxianus* YIT12612 (NBRC0260)

(ii) Pre-Preculture

Pre-preculture: 20 μl of a strain cryopreserved in 20% glycerol was inoculated into 2 ml of a Yeast and Mold (YM) culture medium (1% glucose, 0.5% peptone, 0.3% yeast extract, and 0.3% malt extract) and incubated with shaking at 160 rpm for 24 hours at 30° C.

(2) Analysis of Aroma Components Produced By Bacteria
  (i) Preculture

Preculture: 20 μl of the culture solution obtained from the pre-preculture was inoculated into 2 ml of a whey-containing culture medium supplemented with 1% glucose and incubated with shaking at 160 rpm for 24 hours at 30° C.

As the above described whey-containing culture medium, the supernatant of the culture product which was obtained by culturing *Streptococcus thermophilus* YIT2084 (FERM BP-10879) in a 3% skimmed milk powder-containing culture medium was used. The result of analysis of this supernatant showed that the supernatant contained lactose at an amount of 1.1%, galactose at an amount of 0.4%, and lactic acid at an amount of 0.4%, and had a pH of 4.0.

(ii) Culture

Culture: 50 μl of the preculture solution was inoculated into 5 ml of a whey-containing culture medium supplemented with 1% glucose and incubated with shaking at 160 rpm for 24 hours at 30° C.

(iii) Analysis of Aroma Components

After completion of incubation, a sample was collected and centrifuged at 8,000 rpm for 5 minutes and 2 ml of the supernatant was collected in a 20 ml vial. Then, an aroma component in the culture product was identified by Headspace gas chromatography mass spectrometry (HS-GC-MS) (Tables 1 and 2). Furthermore, the identified aroma component was quantified by HS-GC-Flame Ionization Detector (FID) (Tables 3 and 4). The result is shown in Table 5. Furthermore, sensory analysis of the odor of the culture solution was performed using the criteria described below. The result is shown in Table 5.

(Evaluation Criteria for Sensory Analysis)
5: A complex and fresh fruity aroma is strongly detected.
4: A complex and fresh fruity aroma is detected.
3: A complex and fresh fruity aroma is slightly detected.
2: A complex and fresh fruity aroma is hardly detected.
1: No complex and fresh fruity aroma is detected.

TABLE 1

| HS Conditions: | |
|---|---|
| Device | MPS2-xt |
| Syringe size | 2.5 ml |
| Agitator temperature | 50° C. |
| Agitator speed | 250 rpm |
| Vial equilibration time | 15 min |
| Syringe temperature | 100° C. |
| Injection volume | 1000 μL |
| Injection rate | 200 μL/s |

TABLE 2

| GC-MS Conditions: | |
|---|---|
| System | MS700D (JEOL) |
| Column | InertCap Pure WAX 30 m × 0.25 mm i.d. × 0.25 μm (GL Sciences) |
| Oven temperature | 40° C.-250° C. (10° C./min) |
| Carrier gas | He |
| Flow rate | 0.7 ml/min |
| Injection temperature | 250° C. |
| Split ratio | Splitless |
| MS resolution | 1000 |
| Ionizing current | 300 μA |
| Ionizing voltage | 70 eV |
| Chamber temperature | 250° C. |
| Injection volume | 1 μL |

TABLE 3

| HS Conditions: | |
|---|---|
| Device | Agilent 7697A |
| Loop size (ml) | 5 |
| Oven temperature (° C.) | 50 |
| Loop temperature (° C.) | 110 |
| Transfer line temperature (° C.) | 115 |
| Vial equilibration (min) | 15 |
| Injection time (min) | 1 |

TABLE 4

| GC Conditions: | |
|---|---|
| System | Agilent 7890B |
| Column | InertCap Pure WAX 30 m × 0.25 mm i.d. × 0.25 μm (GL Sciences) |
| Oven temperature | 40° C. (5 min)-10° C./min-250° C. (3 min) |
| Carrier gas | He |
| Flow rate | 3 ml/min |
| Injection temperature | 250° C. |
| Split ratio | 20:1 |
| Split flow rate | 60 ml/min |
| Vial equilibration (min) | 5 |
| Injection time (min) | 1 |

TABLE 5

| Compounds (ppm) | NBRC1290 | NBRC1887 | *Kluyveromyces marxianus* NBRC0260 |
|---|---|---|---|
| Alcohol | | | |
| Isoamyl alcohol | 10.07 | 10.79 | 29.07 |
| Ethyl ester | | | |
| Ethyl benzoate | 1.14 | 1.24 | 0.00 |
| Evaluation by sensory analysis | 5 | 5 | 1 |

A complex and fresh fruity aroma was strongly detected in the culture solutions of the NBRC1290 strain and the NBRC1887 strain. The results of analysis of the aroma components and comparison of the contents of the compounds demonstrated the culture solutions characteristically had a high content of ethyl benzoate. For comparison with these culture solutions, aroma components of the culture solution obtained by culturing a different yeast species (*Kluyveromyces marxianus* NBRC0260 strain) in a whey-containing culture medium were analyzed and evaluated. The result showed the culture solution of the NBRC0260 strain had a strong rose-like aroma but hardly any fruity aroma, and contained no ethyl benzoate.

The culture solutions of the NBRC1290 strain and the NBRC1887 strain and a chemically synthesized product of ethyl benzoate alone in an amount equal to that in the culture solutions were subjected to sensory analysis. A complex aroma which the chemically synthesized product fails in producing was detected in the culture solutions of the NBRC1290 strain and the NBRC1887 strain. Thus, the culture solutions had a better aroma than the chemically synthesized product.

(3) Difference in Yields of Aroma Components By Bacteria Depending on Culture Media An experiment was performed using the NBRC1290 strain and the NBRC1887 strain.

(i) Preculture

Preculture: 20 µl aliquots of the culture solution obtained from the pre-preculture were inoculated into 2 ml of a whey-containing culture medium supplemented with 1% glucose, 2 ml of a YPD culture medium (1% yeast extract, 2% peptone, and 2% glucose), and 2 ml of a YM culture medium (1% glucose, 0.5% peptone, 0.3% yeast extract, and 0.3% malt extract) and incubated with shaking at 160 rpm for 24 hours at 30° C.

(ii) Culture

Culture: 5 ml aliquots of the culture solution obtained from the preculture were inoculated into 2 ml of the whey-containing culture medium supplemented with 1% glucose, 2 ml of the YPD culture medium, and 2 ml of the YM culture medium, and incubated with shaking at 160 rpm for 24 hours at 30° C.

(iii) Analysis of the Content of an Aroma Component

After completion of incubation, the content of an aroma component in the culture product was analyzed by HS-GC-FID (Tables 3 and 4). The result is shown in Table 6. Sensory analysis of the odor of the culture product was also performed using the same criteria as described in Example 1 (2). The result is shown in Table 6.

TABLE 6

|  | NBRC1290 | | | NBRC1887 | | |
| --- | --- | --- | --- | --- | --- | --- |
| Compounds (ppm) | Whey | YPD | YM | Whey | YPD | YM |
| Alcohol | | | | | | |
| Isoamyl alcohol | 17.07 | 242.14 | 70.07 | 7.53 | 235.7 | 98.31 |
| Ethyl ester | | | | | | |
| Ethyl benzoate | 2.69 | 0.10 | 0.09 | 2.78 | 0.00 | 0.11 |
| Evaluation by sensory analysis | 5 | 2 | 2 | 5 | 1 | 2 |

When the NBRC1290 strain and the NBRC1887 strain were cultured in the whey-containing culture media, a complex and fresh fruity aroma was strongly detected in the resulting culture solutions. The culture solutions contained a large quantity of ethyl benzoate. In contrast, when the above described strains were cultured in the YM culture medium and the YPD culture medium, the resulting culture solutions contained ethyl benzoate in some cases, but the content was low and a complex and fresh fruity aroma was hardly detected.

(4) Difference In Yields of an Aroma Component By Bacteria Depending On Culture Conditions An experiment was performed by using the NBRC1887 strain.

(i) Preculture

Preculture: 20 µl of the culture solution obtained from the pre-preculture was inoculated into 2 ml of a whey-containing culture medium supplemented with 1% glucose and incubated with shaking at 160 rpm for 24 hours at 30° C.

(ii) Culture

Culture: 1 ml aliquots of the preculture solution were inoculated into 100 ml of the whey-containing culture medium supplemented with 1% glucose and were incubated with shaking at 160 rpm under the culture conditions of the temperature of 15° C., 20° C., 25° C., and 30° C. Samples were collected after 0, 24, 32, 48, and 56 hours of incubation.

(iii) Analysis of the Content of ethyl benzoate

The content of ethyl benzoate in the culture products was analyzed by HS-GC-FID (Tables 3 and 4). The result is shown in Table 7. Furthermore, sensory analysis of the odor of the culture products was performed using the criteria described below. The result is shown in Table 7.

(Evaluation Criteria for Sensory Analysis)

a: A complex and fresh fruity aroma is strongly detected.
b: A complex and fresh fruity aroma is detected.
c: A complex and fresh fruity aroma is slightly detected but the complexity is low.
d: The odor of other aroma components is strong. The character of the odor is changed and a sake-like odor is detected.
e: No complex and fresh fruity aroma is detected.

TABLE 7

| | Ethyl benzoate (ppm)/Evaluation by sensory analysis | | | | |
| --- | --- | --- | --- | --- | --- |
| | 0 hr | 24 hr | 32 hr | 48 hr | 54 hr |
| 15° C. | 0/e | 0.73/c | 2.48/c | 2.24/c | 2.18/c |
| 20° C. | 0/e | 3.04/a | 2.54/b | 2.06/d | 1.90/d |
| 25° C. | 0/e | 2.48/b | 1.89/b | 1.65/d | 1.67/d |
| 30° C. | 0/e | 2.23/b | 1.72/b | 1.26/d | 1.51/d |

For the incubation at a temperature of 15° C., ethyl benzoate was produced by microbial fermentation. However, the odor of other aroma components was weak, and thus the complexity of the odor of the culture product was low. In contrast, the culture product resulting from incubation at temperatures ranging from 20 to 30° C. had a complex and fresh fruity aroma, that is, the culture product had a good odor. In the case of a culture time of 48 hours or more, the yield of aroma components other than ethyl benzoate increased due to microbial fermentation. Consequently, the odor of the other aroma components became stronger so that the character of the odor was changed and a sake-like odor was detected. Therefore, the preferable culture time was from 24 to 32 hours.

(5) Difference in Contents of ethyl benzoate Resulting from Addition of Benzoic Acid or a Salt thereof to the Culture Medium An experiment was performed by using the NBRC1887 strain.

(i) Preculture

Preculture: 20 µl of the culture solution obtained from the pre-preculture was inoculated into 2 ml of a whey-containing culture medium supplemented with 1% glucose and incubated with shaking at 160 rpm for 24 hours at 30° C.

(ii) Culture

Culture: sodium benzoate was added to 100 ml of the whey-containing culture medium supplemented with 1% glucose to a final concentration of 0.01%. In a similar manner, each of benzoic acid, phenylalanine, and para-hydroxymethylbenzene was added to 100 ml of the whey-containing culture medium supplemented with 1% glucose to obtain the culture medium containing 0.01% benzoic acid, the culture media containing 0.01%, 0.05%, or 0.1% phenylalanine, and the culture media containing 0.01% or 0.05% para-hydroxymethylbenzene. Furthermore, 100 ml of the whey-containing culture medium supplemented with 1% glucose which had no additive was prepared as a control. One-milliliter aliquots of the preculture solution were inoculated into each of the culture media and incubated with shaking at 160 rpm at 30° C. Samples were collected after 0, 24, 32, and 48 hours of incubation.

(iii) Analysis of the Content of ethyl benzoate

The content of ethyl benzoate in the culture products was analyzed by HS-GC-FID (Tables 3 and 4). The result is shown in Table 8.

TABLE 8

The content of ethyl benzoate in each culture solution (ppm)

|  | Control | 0.01% Sodium benzoate | 0.01% Benzoic acid | 0.01% Phenyl-alanine | 0.05% Phenyl-alanine | 0.1% Phenyl-alanine | 0.01% Para-hydroxy-methyl-benzene | 0.05% Para-hydroxy-methyl-benzene |
|---|---|---|---|---|---|---|---|---|
| 0 Hours | 0 | 0 | 0 | 0 | 0 | 0 | 0 | 0 |
| 24 Hours | 2.44 | 3.30 | 2.41 | 2.43 | 2.38 | 2.66 | 0.71 | 0.07 |
| 32 Hours | 3.54 | 12.59 | 15.31 | 3.37 | 3.39 | 3.65 | 2.17 | 0.34 |
| 48 Hours | 2.89 | 27.67 | 23.53 | 2.48 | 2.58 | 2.28 | 2.78 | 2.12 |

The content of ethyl benzoate in the culture products significantly increased when benzoic acid or sodium benzoate was added to the culture medium and the culture time was 32 to 48 hours. The content of ethyl benzoate in the culture products hardly increased when other substances were added to the culture medium.

Preparation Example 1

In reference to the composition shown in Table 9, to a mixture of (5) and (6), were added (1) to (4). The mixture was stirred thoroughly to prepare a toner. This toner had a complex and fresh fruity aroma. In this Example, the culture solution was used after filtration, wherein the culture solution had been obtained by inoculating 1 ml of the preculture solution resulting from preculture in Example 1 (4) into 100 ml of a whey-containing culture medium supplemented with 1% glucose and incubating the culture with shaking at 160 rpm for 24 hours at 20° C.

TABLE 9

| | Raw material | Quantity used (%) |
|---|---|---|
| (1) | Ethanol | 5.0 |
| (2) | 1,3-Butylene glycol | 2.0 |
| (3) | Polyoxyethylene hydrogenated castor oil | 0.05 |
| (4) | Methyl parahydroxybenzoate | 0.1 |

TABLE 9-continued

| | Raw material | Quantity used (%) |
|---|---|---|
| (5) | Culture solution | 10.0 |
| (6) | Distilled water | Balance to 100 |

Preparation Example 2

In reference to the composition shown in Table 10, to (10) were added (7) to (9), and the mixture was heated and then emulsified by adding (1) to (6) thereto at 80° C. The mixture was allowed to cool down to the room temperature to prepare a milky lotion. This milky lotion had a complex and fresh fruity aroma. The culture solution used was the same culture solution as that in Preparation Example 1.

TABLE 10

| | Raw material | Quantity (%) |
|---|---|---|
| (1) | Stearic acid | 2.0 |
| (2) | Liquid paraffin | 5.0 |

TABLE 10-continued

| | Raw material | Quantity (%) |
|---|---|---|
| (3) | Squalane | 2.0 |
| (4) | Sorbitan monostearate | 0.05 |
| (5) | Polyoxyethylene (20) sorbitan monostearate | 2.0 |
| (6) | Butyl parahydroxybenzoate | 0.05 |
| (7) | Glycerin | 2.0 |
| (8) | Methyl parahydroxybenzoate | 0.1 |
| (9) | Culture solution | 3.0 |
| (10) | Distilled water | Balance to 100% |

Preparation Example 3

In reference to the composition shown in Table 11, to (12) were added (9) to (11), and the mixture was heated and then emulsified by adding (1) to (8) thereto at 80° C. The mixture was allowed to cool down to the room temperature to prepare a cream. This cream had a complex and fresh fruity aroma. The culture solution used was the same culture solution as that in Preparation Example 1.

TABLE 11

| | Raw material | Quantity (%) |
|---|---|---|
| (1) | Liquid paraffin | 23.0 |
| (2) | Petrolatum | 7.0 |
| (3) | Cetanol | 1.0 |

TABLE 11-continued

| | Raw material | Quantity (%) |
|---|---|---|
| (4) | Stearic acid | 2.0 |
| (5) | Beeswax | 2.0 |
| (6) | Sorbitan monostearate | 3.5 |
| (7) | Polyoxyethylene (20) sorbitan monostearate | 2.5 |
| (8) | Butyl parahydroxybenzoate | 0.05 |
| (9) | 1,3-Butylene glycol | 1.0 |
| (10) | Methyl parahydroxybenzoate | 0.1 |
| (11) | Culture solution | 3.0 |
| (12) | Distilled water | Balance to 100 |

The invention claimed is:

1. A culture product obtained by culturing a microorganism belonging to the genus *Wickerhamomyces* in a milk component-containing culture medium,
   wherein the microorganism belonging to the genus *Wickerhamomyces* is at least one selected from the group consisting of *Wickerhamomyces pijperi* NBRC1290 and *Wickerhamomyces pijperi* NBRC1887.

2. The culture product according to claim 1, wherein the milk component-containing culture medium is a whey-containing culture medium.

3. The culture product according to claim 1, wherein the milk component-containing culture medium further comprises at least one selected from the group consisting of benzoic acid and a salt thereof.

4. A flavoring composition comprising the culture product according to claim 1.

5. A cosmetic product comprising the culture product according to claim 1.

6. A food or a drink comprising the culture product according to claim 1.

7. A pharmaceutical product comprising the culture product according to claim 1.

8. A method for imparting an aroma to a cosmetic product, a food or a drink, or a pharmaceutical product, the method comprising:
   adding the culture product according to claim 1 to the cosmetic product, food, drink, or pharmaceutical product.

9. A flavoring composition comprising the culture product according to claim 2.

10. A flavoring composition comprising the culture product according to claim 3.

11. A method for imparting an aroma to a cosmetic product, a food or a drink, or a pharmaceutical product, the method comprising:
    adding the culture product according to claim 2 to the cosmetic product, food, drink, or pharmaceutical product.

12. A method for imparting an aroma to a cosmetic product, a food or a drink, or a pharmaceutical product, the method comprising:
    adding the culture product according to claim 3 to the cosmetic product, food, drink, or pharmaceutical product.

* * * * *